(12) United States Patent
Khamis et al.

(10) Patent No.: US 9,364,308 B2
(45) Date of Patent: Jun. 14, 2016

(54) IMPLANT SYSTEMS WITH TENSIONING FEEDBACK

(75) Inventors: Chaouki A. Khamis, Edina, MN (US);
Shawn M. Wignall, Woodbury, MN (US); David J. Kupiecki, Edina, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 210 days.

(21) Appl. No.: 13/520,068

(22) PCT Filed: Dec. 30, 2010

(86) PCT No.: PCT/US2010/062477
§ 371 (c)(1),
(2), (4) Date: Sep. 13, 2012

(87) PCT Pub. No.: WO2011/082287
PCT Pub. Date: Jul. 7, 2011

(65) Prior Publication Data
US 2013/0018219 A1     Jan. 17, 2013

Related U.S. Application Data

(60) Provisional application No. 61/291,238, filed on Dec. 30, 2009.

(51) Int. Cl.
*A61F 2/08* (2006.01)
*A61F 2/02* (2006.01)
*A61F 2/00* (2006.01)

(52) U.S. Cl.
CPC ....... *A61F 2/0045* (2013.01); *A61F 2250/0097* (2013.01)

(58) Field of Classification Search
CPC ............... A61F 2/0045; A61F 2/0063; A61F 2002/0888; A61F 2250/0087; A61F 2250/0078; A61F 2250/0018

USPC .......................................................... 600/37
See application file for complete search history.

(56) References Cited

U.S. PATENT DOCUMENTS 2,738,790 A    3/1956  Todt et al.
3,124,136 A    3/1964  Usher
(Continued)

FOREIGN PATENT DOCUMENTS

AU    2002241673    11/2005
CA    2404459       8/2005
(Continued)

OTHER PUBLICATIONS

Tsuchihara et al., Development of Polymer films that change color in response to tension. National Institute of Advanced Industrial Scinece and Technology. Press Release Nov. 17, 2008. Retrieved on Apr. 30, 2014. Retrieved from internet: http://www.aistgo.jp/aist_e/latest_research/2008/20081117/20081117.html.*

(Continued)

*Primary Examiner* — Charles A Marmor, II
*Assistant Examiner* — Joshua D Lannu
(74) *Attorney, Agent, or Firm* — Skaar Ulbrich Macari, P.A.

(57) ABSTRACT

Pelvic or other types of implants are provided that can include tensioning feedback components or portions, such as color changing polymer materials, such as polyacetylene. The color changing polymer can be included with, coated on or otherwise provided with a portion of slings or implant devices to provide targeted feedback to the user or physician of the tension applied to a particular device. A first color can be used to indicate a first (initial) tension or compression stage, and a second color can be used to indicate tensioning of the device beyond a predefined threshold.

6 Claims, 3 Drawing Sheets

(56) References Cited

U.S. PATENT DOCUMENTS

| | | | |
|---|---|---|---|
| 3,384,073 | A | 5/1968 | Van Winkle, Jr. |
| 3,580,313 | A | 5/1971 | McKnight |
| 3,763,860 | A | 10/1973 | Clarke |
| 3,789,828 | A | 2/1974 | Schulte |
| 3,815,576 | A | 6/1974 | Balaban |
| 4,019,499 | A | 4/1977 | Fitzgerald |
| 4,172,458 | A | 10/1979 | Pereyra |
| 4,246,660 | A | 1/1981 | Wevers |
| 4,509,516 | A | 4/1985 | Richmond |
| 4,548,202 | A | 10/1985 | Duncan |
| 4,632,100 | A | 12/1986 | Somers et al. |
| 4,775,380 | A | 10/1988 | Seedhom et al. |
| 4,857,041 | A | 8/1989 | Annis et al. |
| 4,865,031 | A | 9/1989 | O'Keeffe |
| 4,873,976 | A | 10/1989 | Schreiber |
| 4,920,986 | A | 5/1990 | Biswas |
| 4,938,760 | A | 7/1990 | Burton et al. |
| 4,969,892 | A | 11/1990 | Burton et al. |
| 5,007,894 | A | 4/1991 | Enhorning |
| 5,012,822 | A | 5/1991 | Schwarz |
| 5,013,292 | A | 5/1991 | Lemay |
| 5,013,316 | A | 5/1991 | Goble et al. |
| 5,019,032 | A | 5/1991 | Robertson |
| 5,036,867 | A | 8/1991 | Biswas |
| 5,085,661 | A | 2/1992 | Moss |
| 5,112,344 | A | 5/1992 | Petros |
| 5,123,428 | A | 6/1992 | Schwarz |
| 5,141,520 | A | 8/1992 | Goble et al. |
| 5,209,756 | A | 5/1993 | Seedhom et al. |
| 5,250,033 | A | 10/1993 | Evans et al. |
| 5,256,133 | A | 10/1993 | Spitz |
| 5,269,783 | A | 12/1993 | Sander |
| 5,328,077 | A | 7/1994 | Lou |
| 5,337,736 | A | 8/1994 | Reddy |
| 5,362,294 | A | 11/1994 | Seitzinger |
| 5,368,595 | A | 11/1994 | Lewis |
| 5,370,650 | A | 12/1994 | Tovey et al. |
| 5,370,662 | A | 12/1994 | Stone et al. |
| 5,376,097 | A | 12/1994 | Phillips |
| 5,386,836 | A | 2/1995 | Biswas |
| 5,413,598 | A | 5/1995 | Moreland |
| 5,474,518 | A | 12/1995 | Velazquez |
| 5,474,543 | A | 12/1995 | McKay |
| 5,518,504 | A | 5/1996 | Polyak |
| 5,520,700 | A | 5/1996 | Beyar et al. |
| 5,527,342 | A | 6/1996 | Pietrzak et al. |
| 5,562,689 | A | 10/1996 | Green et al. |
| 5,571,139 | A | 11/1996 | Jenkins, Jr. |
| 5,582,188 | A | 12/1996 | Benderev et al. |
| 5,591,163 | A | 1/1997 | Thompson |
| 5,591,206 | A | 1/1997 | Moufarrege |
| 5,611,515 | A | 3/1997 | Benderev et al. |
| 5,628,756 | A | 5/1997 | Barker, Jr. et al. |
| 5,643,320 | A | 7/1997 | Lower et al. |
| 5,683,349 | A | 11/1997 | Makower et al. |
| 5,697,931 | A | 12/1997 | Thompson |
| 5,709,708 | A | 1/1998 | Thal |
| 5,725,541 | A | 3/1998 | Anspach, III et al. |
| 5,741,282 | A | 4/1998 | Anspach, III et al. |
| 5,782,916 | A | 7/1998 | Pintauro et al. |
| 5,785,640 | A | 7/1998 | Kresch et al. |
| 5,807,403 | A | 9/1998 | Beyar et al. |
| 5,836,314 | A | 11/1998 | Benderev et al. |
| 5,836,315 | A | 11/1998 | Benderev et al. |
| 5,840,011 | A | 11/1998 | Landgrebe et al. |
| 5,842,478 | A | 12/1998 | Benderev et al. |
| 5,860,425 | A | 1/1999 | Benderev et al. |
| 5,899,909 | A | 5/1999 | Claren et al. |
| 5,919,232 | A | 7/1999 | Chaffringeon et al. |
| 5,922,026 | A | 7/1999 | Chin |
| 5,934,283 | A | 8/1999 | Willem et al. |
| 5,944,732 | A | 8/1999 | Raulerson et al. |
| 5,954,057 | A | 9/1999 | Li |
| 5,972,000 | A | 10/1999 | Beyar et al. |
| 5,980,558 | A | 11/1999 | Wiley |
| 5,984,927 | A | 11/1999 | Wenstrom, Jr. |
| 5,988,171 | A | 11/1999 | Sohn et al. |
| 5,997,554 | A | 12/1999 | Thompson |
| 6,010,447 | A | 1/2000 | Kardjian |
| 6,027,523 | A | 2/2000 | Schmieding |
| 6,030,393 | A | 2/2000 | Corlew |
| 6,036,701 | A | 3/2000 | Rosenman |
| 6,039,686 | A | 3/2000 | Kovac |
| 6,042,534 | A | 3/2000 | Gellman et al. |
| 6,042,536 | A | 3/2000 | Tihon et al. |
| 6,042,583 | A | 3/2000 | Thompson et al. |
| 6,048,351 | A | 4/2000 | Gordon et al. |
| 6,050,937 | A | 4/2000 | Benderev |
| 6,053,935 | A | 4/2000 | Brenneman et al. |
| 6,056,688 | A | 5/2000 | Benderev et al. |
| 6,068,591 | A | 5/2000 | Bruckner et al. |
| 6,071,290 | A | 6/2000 | Compton |
| 6,074,341 | A | 6/2000 | Anderson et al. |
| 6,077,216 | A | 6/2000 | Benderev et al. |
| 6,099,538 | A | 8/2000 | Moses |
| 6,099,551 | A | 8/2000 | Gabbay |
| 6,099,552 | A | 8/2000 | Adams |
| 6,106,545 | A | 8/2000 | Egan |
| 6,110,101 | A | 8/2000 | Tihon et al. |
| 6,117,067 | A | 9/2000 | Gil-Vernet |
| 6,127,597 | A | 10/2000 | Beyar et al. |
| 6,168,611 | B1 | 1/2001 | Risvi |
| 6,200,330 | B1 | 3/2001 | Benderev et al. |
| 6,221,005 | B1 | 4/2001 | Bruckner et al. |
| 6,241,736 | B1 | 6/2001 | Sater et al. |
| 6,264,676 | B1 | 7/2001 | Gellman et al. |
| 6,273,852 | B1 | 8/2001 | Lehe et al. |
| 6,302,840 | B1 | 10/2001 | Benderev |
| 6,306,079 | B1 | 10/2001 | Trabucco |
| 6,322,492 | B1 | 11/2001 | Kovac |
| 6,328,686 | B1 | 12/2001 | Kovac |
| 6,328,744 | B1 | 12/2001 | Harari et al. |
| 6,334,446 | B1 | 1/2002 | Beyar |
| 6,352,553 | B1 | 3/2002 | van de Burg et al. |
| 6,382,214 | B1 | 5/2002 | Raz et al. |
| 6,387,041 | B1 | 5/2002 | Harari et al. |
| 6,406,423 | B1 | 6/2002 | Scetbon |
| 6,406,480 | B1 | 6/2002 | Beyar et al. |
| 6,423,080 | B1 | 7/2002 | Gellman et al. |
| 6,451,024 | B1 | 9/2002 | Thompson et al. |
| 6,475,139 | B1 | 11/2002 | Miller |
| 6,478,727 | B2 | 11/2002 | Scetbon |
| 6,482,214 | B1 | 11/2002 | Sidor, Jr. et al. |
| 6,491,703 | B1 | 12/2002 | Ulmsten |
| 6,502,578 | B2 | 1/2003 | Raz et al. |
| 6,506,190 | B1 | 1/2003 | Walshe |
| 6,530,943 | B1 | 3/2003 | Hoepffner et al. |
| 6,575,897 | B1 | 6/2003 | Ory |
| 6,582,443 | B2 | 6/2003 | Cabak et al. |
| 6,592,515 | B2 | 7/2003 | Thierfelder |
| 6,592,610 | B2 | 7/2003 | Beyar |
| 6,596,001 | B2 | 7/2003 | Stormby et al. |
| 6,599,235 | B2 | 7/2003 | Kovac |
| 6,599,323 | B2 | 7/2003 | Melican et al. |
| 6,602,260 | B2 | 8/2003 | Harari et al. |
| 6,612,977 | B2 | 9/2003 | Staskin |
| 6,638,210 | B2 | 10/2003 | Berger |
| 6,638,211 | B2 | 10/2003 | Suslian et al. |
| 6,638,284 | B1 | 10/2003 | Rousseau et al. |
| 6,641,524 | B2 | 11/2003 | Kovac |
| 6,641,525 | B2 | 11/2003 | Rocheleau |
| 6,648,921 | B2 | 11/2003 | Anderson |
| 6,652,450 | B2 | 11/2003 | Neisz et al. |
| 6,673,010 | B2 | 1/2004 | Skiba et al. |
| 6,685,629 | B2 | 2/2004 | Therin |
| 6,689,047 | B2 | 2/2004 | Gellman et al. |
| 6,691,711 | B2 | 2/2004 | Raz |
| 6,699,175 | B2 | 3/2004 | Miller |
| 6,702,827 | B1 | 3/2004 | Lund |
| 6,752,814 | B2 | 6/2004 | Gellman et al. |
| 6,755,781 | B2 | 6/2004 | Gellman |
| 6,802,807 | B2 | 10/2004 | Anderson |
| 6,830,052 | B2 | 12/2004 | Carter et al. |
| 6,881,184 | B2 | 4/2005 | Zappala |

(56) References Cited

U.S. PATENT DOCUMENTS

| | | | |
|---|---|---|---|
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,762,942 B2 | 7/2010 | Neisz et al. |
| 7,766,926 B2 | 8/2010 | Bosley et al. |
| 7,789,821 B2 | 9/2010 | Browning |
| 7,927,342 B2 | 4/2011 | Rioux |
| 7,981,024 B2 | 7/2011 | Levy |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz et al. |
| 2003/0004581 A1 | 1/2003 | Rousseau |
| 2003/0010929 A1 | 1/2003 | Prieve et al. |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0010078 A1* | 1/2005 | Jamiolkowski et al. ........ 600/30 |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Iandgrebe |
| 2007/0173864 A1 | 7/2007 | Chu |
| 2008/0039678 A1 | 2/2008 | Montpetit et al. |
| 2008/0140251 A1 | 6/2008 | Staskin et al. |
| 2008/0177132 A1* | 7/2008 | Alinsod et al. ................. 600/37 |
| 2008/0196729 A1* | 8/2008 | Browning ..................... 128/834 |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |
| 2010/0022822 A1 | 1/2010 | Walshe |
| 2010/0261950 A1 | 10/2010 | Lund |
| 2011/0124954 A1 | 5/2011 | Ogdahl et al. |
| 2012/0016185 A1 | 1/2012 | Sherts et al. |

FOREIGN PATENT DOCUMENTS

| | | |
|---|---|---|
| DE | 4220283 C2 | 5/1994 |
| DE | 19544162 | 4/1997 |
| DE | 10211360 | 9/2003 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9747244 A1 | 12/1997 |
| WO | WO9819606 A1 | 5/1998 |

(56) References Cited

FOREIGN PATENT DOCUMENTS

| | | |
|---|---|---|
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO99/59477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

Aldridge, Albert, "Transplantation of Fascia for Relief of Urinary Stress Incontinence," Am. J. Obstetrics and Gynecology, V.44, pp. 398-411.

Amundsen et al., "Anatomical correction of vaginal vault prolapse by uterosacral ligament fixation in women who also require a pubovaginal sling," The J. of Urology, vol. 169, 1770-1776, May 2003.

Araki, Tohru, et. al., "The Loop-Loosening Procedure for Urination Difficulties After Stamey Suspension of the Vesical Neck," J. of Urology, vol. 144, Aug. 1990, pp. 319-323.

Asmussen et. al., "Simultaneous Urethro-Cystometry with a New Technique," Scand. J. Urol. Nephrol 10:7-11, 1976, pp. 7-10.

Beck et. al., "Treatment of Urinary Stress Incontinence with Anterior Colporrhapy," J. of Am. Col. of Obstetricians and Gynecologists, V.59, No. 3, Mar. 1982, pp. 269-.

Benderev, Theodore, "A Modified Percutaneous Outpatient Bladder Neck Suspension System," The J. of Urology, vol. 152, Dec. 1994, pp. 2316-2320.

Benderev, Theodore, "Anchor Fixation and Other Modifications of Endoscopic Bladder Neck Suspension," Urology, vol. 40, No. 5, Nov. 1992, pp. 409-419.

Bergman, et. al., "Three Surgical Procedures for Genuine Stress Incontinence: Five-Year Follow-up of a Prospective Randomized Study," Am. J. Obstetrics and Gynecology, vol. 173, No. 1, pp. 66-7.1.

Blaivas et. al., "Pubovaginal Fascial Sling for the Treatment of Complicated Stress Urinary Incontinence," the J. of Urology, vol. 145, Jun. 1991, pp. 1214-1218.

Blaivas et. al., "Commentary: Pubovaginal Sling Procedure," Surgery for Female Urinary Incontinence, pp. 93-102.

Blaivas et. al., "Type III Stress Urinary Incontinence: Importance of Proper Diagnosis and Treatment," Gynecology and Obstetrics, pp. 473-476.

Zimmern et al., "Four-Corner bladder neck suspension," Vaginal Surgery for the Urologist, vol. 2, No. 1 pp. 29-37 (1994).

Heit et al., "Predicting treatment choice for patients with pelvic organ prolapse," The Am. College of Obstet. & Gyn., vol. 101, No. 6, Jun. 2003.

Julian, Thomas, "The efficacy of Marlex mesh in the repair of severe, recurrent vaginal prolapse of the anterior midvaginal wall," Am. J. Obstet. Gynecol. vol. 175, No. 6, pp. 1471-1476 (1996).

Karram et al., "Surgical Treatment of Vaginal Vault Prolapse," Urogynecology and reconstructive pelvic surgery, Mosby (1999).

Luber, et al., "The demographics of pelvic floor disorders: current observations and future projections," Am. J. Obstet. Gynecol. vol. 184, No. 7, pp. 1496-1504 (2001).

Mage, Ph., "L-interposition d'un treillis synthetique dans la cure par voie vaginale des prolapses genitaux," Technique chirurgicale, J. Gynecol. Obstet. Reprod. 1999:28:825-829.

Marchionni, et al., "True incidence of vaginal vault prolapse: thirteen years of experience," J. of Reproductive Medicine, vol. 44, No. 8, pp. 679-685 (1999).

Migliari et al., "Tension-free vaginal mesh repair for anterior vaginal wall prolapse," Eur. Urol. 2000;38:151-155.

Morley et al., "Sacrospinous ligament fixation for eversion of the vagina," Arm J. Obstet. Gynecol., vol. 158, No. 4, pp. 871-881 (1988).

Morley, Patrick, "Vaginal reconstruction of a complete vaginal prolapse: the transobturator repair," Journal of Urology, vol. 169 (4) supplement, p. 183 (2003).

Nicita, Giulio, "A new operation for genitourinary prolapse," The Journal of Urology, vol. 160, 741-745 (1998).

Paraiso, et al., "Laparoscopic surgery for enterocele, vaginal apex prolapse and rectocele," Int. Urogynecol. J. 10:223-239 (1990).

Paraiso, et al., "Pelvic support defects and visceral and sexual function in women treated with sacrospinous ligament suspension and pelvic reconstruction," Am. J. Obstet. & Gyne. vol. 175, No. 6 (1996).

Petros, P.E., "Vault Prolapse II: restoration of dynamic vaginal supports by infracoccygeal sacropexy, and axial day-case vaginal procedure," Int. Urogynecol. J. (2001) 12:296-303.

(56) References Cited

OTHER PUBLICATIONS

Petros, et al., "The posterior fornix syndrome: a multiple symptom complex of pelvic pain and abnormal urinary symptoms deriving from laxity in the posterior fornix of vagina," Scand. J. Urol. Nephrol. Suppl. No. 153, pp. 89-95 (1993).
Richter, Kurt, "Massive eversion of the vagina: pathogenesis, diagnosis, and therapy of the 'true' prolapse of the vaginal stump," Clinical Obstet. & Gyne., vol. 25, No. 4, pp. 897-911 (1982).
Sanz et al., "Modification of abdominal sacrocolpopexy using a suture anchor system," Journal of Reproductive Medicine, vol. 48, No. 7, pp. 496-501 (2003).
Subak et al., "Cost of pelvic organ prolapse surgery in the United States," Am. College Obstet. & Gyne., vol. 98, No. 4, pp. 464-452 (2001).
Sullivan et al., "Total pelvic mesh repair," Dis Colon Rectum, vol. 44, No. 6 pp. 857-864 (2001).
Swift et al., "Case-control study of etiologic factors in the development of severe pelvic organ prolapse," Int. Urogynecol. J. 12:187-192 (2001).
Visco et al., "Vaginal mesh erosion after abdominal sacral colpopexy," Am. J. Obstet. Gynecol. vol. 184, No. 3, pp. 297-303 (2001).
Bryans et. al. "Marlex Gauze Hammock Sling Operation with Cooper's Ligament Attachment in the Management of Recurrent Urinary Stress Incontinence," Am. J. Obstetrics and Gynecology, vol.
Burch, John C., "Urethrovaginal fixation to Cooper's ligament for correction of stress incontinence, cystocele, and prolapse," Am. J. Obstetrics and Gynecology, vol. 31, No. 2, Feb. 1961.
Cervigni et al., "The use of synthetics in the treatment of pelvic organ prolapse," Current Opinion in Urology 2011, 11:429-435.
Conquy, Dophle, "Le point sur L'incontinence urinaire," Expertise et practiques en urologie, No. 3, 1998.
Das et al., "Laparoscopic colpo-suspension," J. of Urology, vol. 154, pp. 1119-1121, Sep. 1995.
DeLancey, John, "Structural support of the urethra as it relates to stress urinary incontinence: the hammock hypothesis," Am. J. Obstetrics and Gynecology, vol. 170, No. 6, Jun. 1994, pp. 1713-1723.
Eglin et al., Transobturator subvesical mesh: tolerance and short-term results of a 103 case continuous series, Service de gynecologic clinque Dhampeau 32 (Nov. 2002).
Enzelsberger et al., "Urodynamic and radiologic parameters before and after loop surgery for recurrent urinary stress incontinence," Acta. Obstet. Gynecol. Scand., 1990; 69:51-54.
Eriksen et al., "Long-term effectiveness of the Burch colposuspension in female urinary stress incontinence," Acta. Obstet. Gynecol. Scand., 1990; 69:45-50.
Falconer et al., "Clinical outcome and changes in connective tissue metabolism after intravaginal slingplasty in stress incontinent women," Int. Urogynecol. J. (1996) 7:133-137.
Farnsworth, B. N., "Posterior intravaginal slingplasty (infracoccygeal sacropexy) for severe posthysterectomy and vaginal vault prolapse—a preliminary report on efficacy and safety," Int. Urogynecol J (2002) 13:4-8.
Gilja et al., "A modifies raz bladder neck suspension operation (transvaginal burch)," the J. of Urology, vol. 153, 1455-1457, May 1995.
Gittes et al., "No-incision pubovaginal suspension for stress incontinence," The J. of Urology, vol. 138 (1987), pp. 568-570.
Gynecare TVT, "The tension-free solution to female incontinence," ICS/IUGA Symp. 2002.
Hamilton et al., "Procedures for urinary incontinence in the United States, 1979-1997," Am. J. Obstet. Gynecol. vol. 189, No. 1, pp. 70-75 2003.
Handa et al., "Banked Human fascia lata for the suburethral sling procedure: a preliminary report," Obstetrics & Gynecology, vol. 88, No. 6, pp. 1045-1050, Dec. 1996.

Henriksson et al., "A urodynamic evaluation of the effects of abdominal urethrocystopexy and vaginal sling urethroplasty in women with stress incontinence," Am. J. Obstet. Gynecol., vol. 131, No. 1, pp. 77-83, May 1978.
Hodgkinson et al., "Urinary stress incontinence in the female: III. Round-ligament technic for retropubic suspension of the urethra," Obstetrics & Gynecology, vol. 10, No. 5 (1957).
Holschneider et al., "The modified pereyra procedure in recurrent stress urinary incontinence: a 15 year review," Obstetrics & Gynecology, vol. 83, No. 4 pp. 573-579 (1994).
Ingelman-Sundberg, "Surgical treatment of female urinary stress incontinence," Contr. Gynec. Obstet., vol. 10 pp. 51-69 (1983).
Klutke et al., "The anatomy of stress incontinence: magnetic resonance imaging of the female bladder neck and urethra," The J. or Urology, vol. 149, pp. 563-567 (1990).
Klutke et al., "Instruments & Methods: transvaginal bladder neck suspension to cooper's ligament: a modified pereyra procedure," Obstetrics & Gynecology, vol. 88, No. 2, pp. 293-297 (1996).
Leach et al., "Female stress urinary incontinence clinical guidelines panel summary report on surgical management of female stress urinary incontinence," Am. Urological Assc., vol. 158, 875-880 (1997).
Loughlin et al., "Review of an 8-year experience with modifications of endoscopic suspension of the bladder neck for female stress urinary incontinence," The Journal of Urology, vol. 143, pp. 3-4 (1990).
Marshall et al., "The correction of stress incontinence by simple vesicourethral suspension," pp. 509-514.
McGuire, Edward, "Abdominal procedure for stress incontinence," Urologic Clinics of North America, vol. 12 No. 5, pp. 285-291 (1985).
McKiel et al., "Marshall-Marchetti procedure: modifications," The Journal of Urology, vol. 96 (1966).
O'Donnell, Pat, "Combined Raz urethral suspension and McGuire pubovaginal sling for treatment of complicated stress urinary incontinence," The J. of the Ark. Med. Society, vol. 88, No. 8, pp. 389-392 (1992).
Parra et al., "Experience with a simplified technique for the treatment of female stress urinary incontinence," British J. of Urology, vol. 68:615-617 (1990).
Pereyra, Armand, "A simplified surgical procedure for the correction of stress incontinence in women," West. J. Obst. & Gynec., Jul./Aug. (1959).
Pereyra, Armand, "Pubourethral supports in perspective: modified pereyra procedure of urinary incontinence," Obstet. & Gyne. vol. 59. No. 5 (1992).
Petros et al., "The autogenic ligament procedure: a technique for planned formation of an artificial neo-ligament," Acta Obstet Gynecol Scand, 69 Suppl. 153:43-51 (1990).
Petros et al., "Cough transmission ratio: an indicator of suburethral vaginal wall tension rather than urethral closure?", Acta Obstet Gynecol Scand, 69 Suppl. 153:43-51 (1990).
Petros et al., "Cure of stress incontinence by repair of external anal sphincter," Acta Obstet Gynecol Scand, 69 Suppl. 153:75 (1990).
Petros et al., "Non stress non urge female urinary incontinence—diagnosis and cure: a preliminary report," Acta Obstet Gynecol Scand, 69 Suppl. 153:69-70 (1990).
Petros et al., "The role of a lax posterior vaginal fornix in the causation of stress and urgency symptoms: a preliminary report," Acta Obstet Gynecol Scand, 69 Suppl. 153:71-73 (1990).
Petros et al., "The tethered vagina syndrome, post surgical incontinence and I-plasty operation for sure," Acta Obstet Gynecol Scand, 69 Suppl. 153:63-67 (1990).
Petros et al., "Bladder instability in women: a premature activation of the micturition reflex," Neurourology and Urodynamics, 12:235-239 (1993).
Petros et al., "Urethral pressure increase on effort originates from within the urethra, and continence from musculovaginal closure," Neurourology and Urodynamics, 14:337-350 (1995).
Petros et al., "An analysis of rapid pad testing and the history for the diagnosis of stress incontinence," Acta Obstet Gynecol Scand, 71:529-536 (1992).
Petros et al., "An integral theory of female urinary incontinence," Acta Obstet Gynecol Scand, 69 Suppl. 153:7-31 (1990).

(56) References Cited

OTHER PUBLICATIONS

Petros et al., "The tuck procedure: a simplified vaginal repair for treatment of female urinary incontinence," Acta Obstet Gynecol Scand, 69 Suppl. 153:41-42 (1990).
Petros et al., "Anchoring the midurethra restores bladder-neck anatomy and continence," The Lancet, vol. 354 (1999).
Petros et al., "The development of the intravaginal slingplasty procedure: IVS II (with bilateral tucks," Scand. J. Urol. Nephrol. Suppl. No. 153:61-69 (1993).
Petros et al., "Part IV: Surgical applications of the theory—Development of the intravaginal sling plasty (IVS) procedure," Scand. J. Urol. Nephrol. Suppl. No. 153:53-57 (1993).
Petros et al., "The free graft procedure for the cure of the tethered vagina syndrome," Scand. J. Urol. Nephrol. Suppl. No. 153:85-89 (1993).
Petros et al., "An anatomical basis for success and failure of female incontinence surgery," Scand. J. Urol. Nephrol. Suppl. No. 153:55-61 (1993).
Petros et al., "Part II. The biomechanics of vaginal tissue and supporting ligaments with special relevance to the pathogenesis of female urinary incontinence," Scand. J. Urol. Nephrol. Suppl. No. 153:29-31 (1993).
Petros et al., "The further development of the intravaginal slingplasty procedure: IVS IV—(with double-brested unattached vaginal flap repair and free vaginal tapes)," Scand. J. Urol. Nephrol. Suppl. No. 153:73-80 (1993).
Petros et al., "The further development of the intravaginal slingplasty procedure: IVS V—(with double-brested unattached vaginal flap repair and free vaginal tapes)," Scand. J. Urol. Nephrol. Suppl. No. 153:77-81 (1993).
Petros et al., "Further development of the intravaginal slingplasty procedure—IVS III (with midline tuck)," Scand. J. Urol. Nephrol. Suppl. No. 153:69-73 (1993).
Petros et al., "Part III. Surgical principles deriving from the theory," Scand. J. Urol. Nephrol. Suppl. No. 153:41-53 (1993).
Petros et al., "Part I. Theoretical, morphological, radiological correlations and clinical perspective," Scand. J. Urol. Nephrol. Suppl. No. 153:5-29 (1993).
Raz et al., "The Raz bladder neck suspension: results in 206 patients," The Journal of Urology, pp. 845-846 (1992).
Raz et al., "Modified bladder neck suspension for female stress incontinence," Urology, vol. XVII, No. 1, pp. 82-86 (1981).
Richardson et al., "Delayed reaction to the Dacron buttress used in urethropexy," vol. 29, No. 9, pp. 690-694 (1984).
Roberts, Henry, "Cystourethrography in Women," Cystourethrography in Women, vol. XXV No. 293, pp. 253-260 (1952).
Seim et al., "A study of female urinary incontinence in general practice," Scand. J. Urol. Nephrol 30;465-471 (1996).
Sloan et al., "Stress incontinence of urine: a retrospective study of the complications and late results of simple suprapubic suburethral fascial slings," The Journal of Urology, vol. 110, pp. 533-537 (1953).
Spencer et al., "A comparison of endoscopic suspension of the vesical neck with suprapubic vesicourethropexy for treatment of stress urinary incontinence," The Journal of Urology, vol. 137, pp. 411-416 (1987).
Stamey, Thomas, "Endoscopic suspension of the vesical neck for urinary incontinence in females," Am. Surg. pp. 465-472 (1980).
Stanton, Stuart, "Suprapubic approaches for stress incontinence in women," JAGS 38;348-351 (1990).
Studdiford, William, "Transplantation of abdominal fascia for the relief of urinary stress incontinence," Am. J. Obst & Gyne. vol. 47, pp. 764-776 (1994).
Tyco Heathcare, "IVS Tunneller," ICS/IUGA Symp. (2002).
Tyco Heathcare, "IVS Tunneller," ICS/IUGA Symp. (2001).
Ulmsten et al., "The unstable female urethra," Am. J. Obstet & Gynecol. vol. 144, No. 1 (1982).
Ulmsten et al., "Different biochemical composition of connective tissue in continent and stress incontinent women," Acta Obstet. Gynecol. Scand. 66:455-457 (1987).
Ulmsten et al., "Female urinary incontinence—a symptom, not a urodynamic disease. Some theoretical and practical aspect of the diagnosis a treatment of female urinary incontinence," Int. Urogynecology J. 6:2-3 (1995).
Ulmsten et al., "An ambulatory surgical procedure under local anesthesia for treatment of female urinary incontinence," Int. Urogynecology J. 7:81-86 (1996).
Ulmsten et al., "A multicenter study of tension-free vaginal tape (TVT) for surgical treatment of stress urinary incontinence," Int. Urogynecology J. 9:210-213 (1998).
Ulmsten et al., "A three-year follow up of tension free vaginal tape for surgical treatment of female stress urinary incontinence," British Journal of Obstetrics and Gynaecology, vol. 106 pp. 345-350 (1999).
Waxman et al., "Advanced urologic surgery for urinary incontinence," The female Patient, vol. 21, pp. 93-101 (1996).
Webster et al., "Voiding dysfunction following cystourethropexy: its evaluation and management," The Journal of Urology vol. 144, pp. 670-674 (1990).
Webster, George, "Female Urinary Incontinence," Urologic Surgery, $3^{rd}$ Ed., pp. 665-680 (1983).
Winter, Chester, "Peripubic urethropexy for urinary stress incontinence in women," Urology, vol. XX No. 4, pp. 408-412 (1982).
Woodside et al., "Suprapubic endoscopic vesical neck suspension for the management of urinary incontinence in myelodysplastic girls," The Journal of Urology vol. 135, pp. 97-101 (1986).
Zacharin, Robert, "The suspensory mechanism of the female urethra," Journal of Anatomy, vol. 97, Part 3, pp. 423-430 (1963).
Weber et al., "Anterior vaginal prolapse review of anatomy and techniques or surgical repair," Obstet. & Gyne., vol. 89, No. 2, pp. 310-318 (1997).
Winters et al., "Abdominal sacral colpopexy and abdominals enterocele repair in the management of vaginal vault prolapse," Urology 56 (Suppl. 6A) pp. 56-64(2000).

\* cited by examiner

IMPLANT SYSTEMS WITH TENSIONING FEEDBACK

PRIORITY

This Application claims priority to and the benefit of U.S. Provisional Application No. 61/291,238, filed Dec. 30, 2009, which is incorporated herein by reference in its entirety.

FIELD OF THE INVENTION

The present invention relates generally to surgical methods and apparatus and, more specifically, to surgically implantable mesh or sling devices with tensioning feedback features, portions or components.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implantable mesh that can be used to treat incontinence, and/or pelvic organ prolapse and other conditions.

SUMMARY OF THE INVENTION

The present invention describes pelvic implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include tensioning feedback components or portions, such as color changing polymer materials.

Such color changing polymer material, such as polyacetylene, can be included with, coated on or otherwise provided with a portion of slings or implant devices to provide targeted feedback to the user or physician of the tension applied to a particular device. A first color can be used to indicate a first tension or compression stage, and a second color can be used to indicate tensioning of the device beyond a predefined threshold. In certain embodiments, the color changing polymer is capable of returning to the first color upon elimination of the tension and return of the device portion to the original compression stage. As such, the color changing polymer can be reversible to provide a very useful and real-time indicator of tension and compression on the implant device or device portion.

The color changing polymer can be used to construct all or a part of an implant device (e.g., prolapse mesh, incontinence sling, etc.). In those embodiments where the color changing polymer is utilized to construct only part of the implant device, the polymer can be included with or used to define edges, end portions and other specific device portions typically under tension, or where tension is relative to the implants effectiveness, support functioning, and performance. In certain embodiments, the color changing polymer is provided as a coating on particular implant portions, or defines one or more filaments or members defining the implant or mesh device.

DETAILED DESCRIPTION OF PREFERRED EMBODIMENTS

Figure 1:
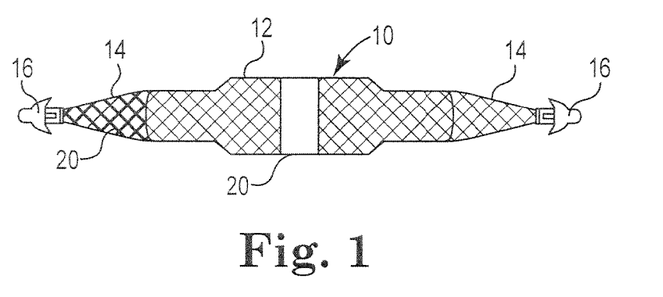
FIG. 1 shows a top view of an elongate sling implant provided with a color changing polymer in accordance with embodiments of the present invention.
Figure 2:
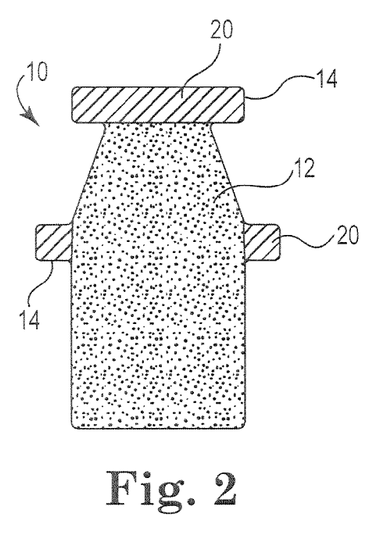
FIGS. 2-4 show a top view of pelvic implants (e.g., prolapse repair) provided with a color changing polymer in accordance with embodiments of the present invention.
Figure 3:
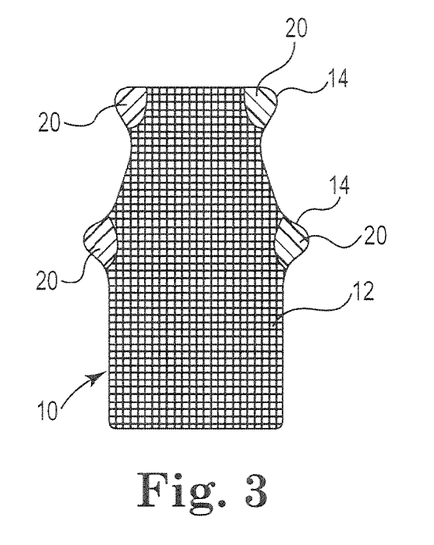
Figure 4:
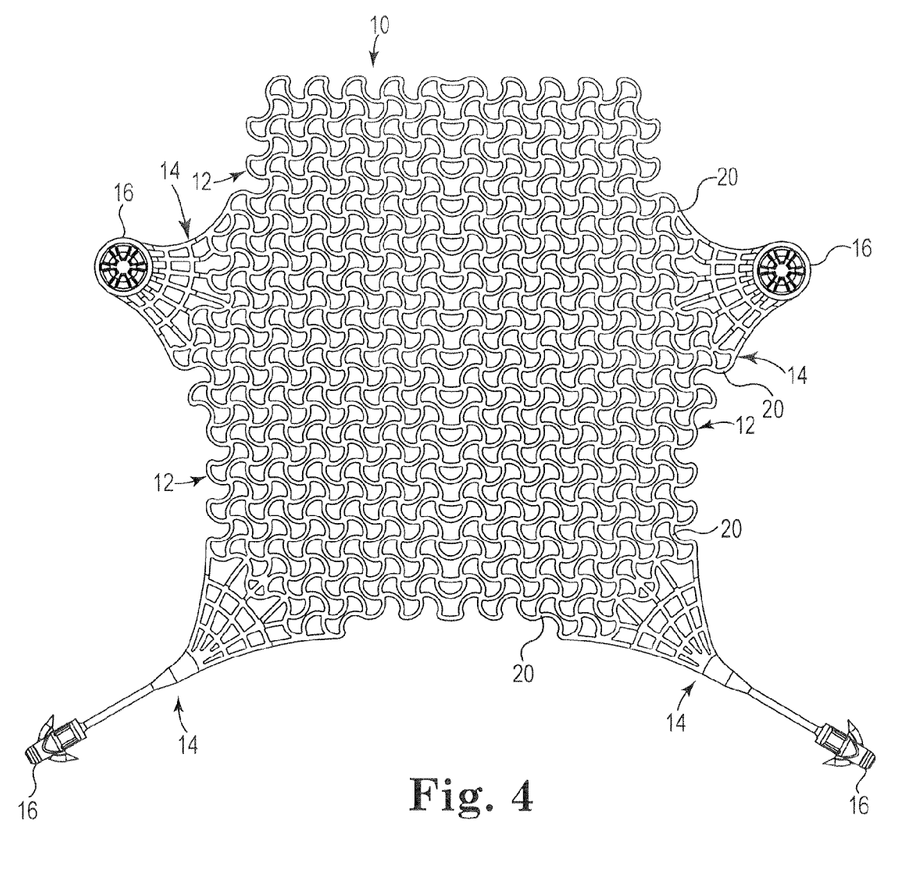
Figure 5:
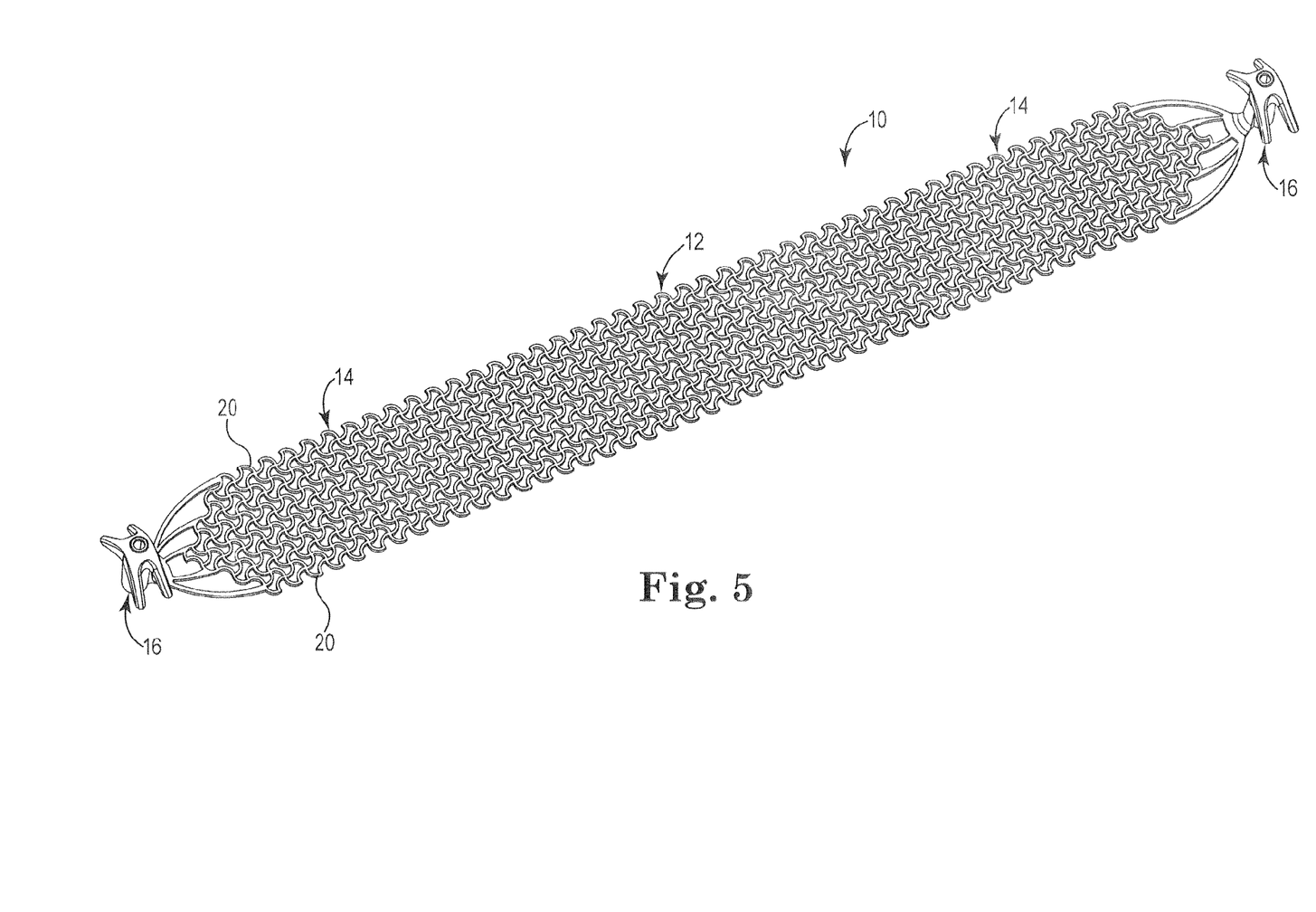
FIG. 5 is a perspective view of an elongate sling implant provided with a color changing polymer in accordance with embodiments of the present invention.

Referring generally to FIGS. 1-5, various embodiments of implantable implant or mesh systems 10 and methods are shown. In general, the implant systems 10 can include a support portion 12 and extension portions 14. Further, anchors 16 or other fixation devices can be included at one or more of the extension portions 14. Various portions of the implant systems 10 can be constructed of polymer materials, such as a thin film or sheet material of polypropylene, polyethylene, fluoropolymers or like compatible materials. The implant systems 10 can be employed to treat incontinence, pelvic prolapse, or like conditions or defects. Various embodiments can be further employed to treat hernias, orthopedic conditions, and other health and wellness issues or problems.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2010/027796 WO 2007/097994, and U.S. Patent Publication Nos. 2010/0261955, 2002/0151762 and 2002/0147382. Accordingly, the above-identified disclosures are fully incorporated herein by reference in their entirety.

In one embodiment of the implant slings or prolapse systems, a unique color changing polymer 20, film, material or coating, is used to construct or is otherwise incorporated with at least a portion of the sling or implant system 10 to provide a change in colors of the material upon defined tension or compression loads. Molding, extrusion, die casting, weaving and like manufacturing or implant formation methods are envisioned for providing the polymer 20 with one or more portions of the implants 10. The shaded or bold areas or portions in the implants of the figures are generally used to indicate the presence of the color changing polymer 20. Indication of the polymer 20 in specific locations or portions of the implants 10 is for demonstrative purposes only. The polymer 20 can be included or provided with the implants 10 at any portion, component or area where tension or compression feedback is desired. In certain embodiments, the entire construct of the implant 10 (portions 12, 14) can include the polymer 20, or be constructed of the polymer 20.

The polymer 20 can be a known polyacetylene (or other known materials adapted to change colors in response to changes in applied tension) that includes properties whereby the polymer will change color under tension or compression. Such color changing polymer material, such as polyacetylene, can be included with, coated on or otherwise provided with a portion of slings or implant devices to provide targeted feedback to the user or physician of the tension applied to a particular device.

As research has indicated, polymerization of acetylene substituted with a substituted phenyl group using [Rh(norbornadiene)Cl]2 as a catalyst. Measurement of the ultraviolet-visible absorption spectrum may increase in absorption from approximately 500 to 600 nm. Removal of the tension and contracting the film can lead to the return of the color of the film from red to yellow, such that the change in color due to stretching and contracting is reversible. Disclosure of such details can be found in *Development of Polymer Films that Change Color in Response to Tension: Easy visualization of mechanical force*, National Institute of Advanced Industrial Science and Technology (AIST) Press Release, Oct. 7, 2008, which is hereby incorporated herein in its entirety.

A first color (e.g., yellow) can be used to indicate a first tension or compression state, with the polymer 20 at an initial non-tensioned condition. A second color (e.g., red) can be used or triggered to indicate tensioning of the device beyond a predefined threshold. In certain embodiments, the color changing polymer 20 is capable of returning to the first color upon elimination of the tension and return of the device portion to the original compressed or non-tensioned condition. As such, the color changing polymer 20 can be reversible to provide a very useful and real-time indicator of tension and compression on the implant device or device portion.

The color changing polymer 20 can be used to construct all or a part of the implant device 10 (e.g., prolapse mesh, incontinence sling, etc.). In those embodiments where the color changing polymer 20 is utilized to construct only part of the implant device (e.g., FIGS. 2-3), the polymer can be included with or used to define edges, end portions and other specific device portions typically under tension, or where tension is relative or important to the implants effectiveness, support functionality, and performance.

In certain embodiments, the color changing polymer 20 is provided as a coating on particular implant portions. In other embodiments, the polymer 20 is provided with or defines one or more filaments, struts or like members of a mesh implant. As shown generally in FIGS. 1, and 4-5, the polymer 20 filaments or struts can be provided at any select portion or section of the corresponding implant 10.

In certain embodiments, a strip of such polymer 20 can be incorporated with an implant sheath or sleeve, such as those disclosed in the previously-incorporated references. The polymer 20 can be incorporated along a longitudinal length, transversely, or a combination thereof.

When the sling or implant is tensioned, the polymer 20 is also placed under tension and will change color. The color change (Which is generally reversible) provides instant feedback to the user as to the level of tensioning achieved. The color level can be developed and validated to provide implanting physicians with a consistent level of tensioning and a highly effective level of tensioning upon deployment of the sling or implant. These tensioning colors can be calibrated to correspond to predefined tensioning levels in accordance with specific applications of the present invention. Further, each color utilized with the tensioning feedback features can be calibrated or noted to define a specific level of tension to promote accuracy, uniformity and consistency across applications or uses.

Further, accessories adapted for interfacing or use with a sling or implant device 10, such as a clamp or grasper, insertion tool or needle, anchors, sutures, eyelets, grommets, to name a few, can include color changing polymer materials integrated or provided therewith. The systems 10, their various components, structures, features, materials and methods may have a number of suitable configurations as shown and described in the previously-incorporated references. Various methods and tools for introducing, deploying, anchoring and manipulating implants to treat incontinence and prolapse as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An implant device for treating prolapse in a patient, comprising:
    a central support portion;
    four spaced arm portions constructed of a mesh material and extending from the central portion; and
    a color changing polymer portion provided with a plurality of mesh filaments on each of the four spaced arm portions to provide tensioning feedback, and wherein the color changing polymer is directly adjacent to the central support portion which does not include the color changing polymer portion, with the color changing polymer portion configured to change colors at a predefined tensioning feedback level.

2. The implant of claim 1, wherein the color changing polymer includes at least a polyacetylene material.

3. The implant of claim 1, wherein the color changing polymer portion is a polymer coating.

4. The implant of claim 1, wherein the color changing polymer portion provides tensioning feedback by displaying a first color in an initial condition and a second color when placed under tension.

5. The implant of claim 4, wherein the color changing polymer portion returns to the first color when compressed to the initial condition.

6. The implant of claim 1, further including one or more arm tissue anchors.

\* \* \* \* \*